united States Patent [19]
Caspari

[11] 4,085,053
[45] Apr. 18, 1978

[54] METAL DITHIOPHOSPHATE PROCESS AND/COMPOSITION
[75] Inventor: Gunter Caspari, Wheaton, Ill.
[73] Assignee: Standard Oil Company (Indiana), Chicago, Ill.
[21] Appl. No.: 799,673
[22] Filed: May 23, 1977
[51] Int. Cl.$^2$ .................. C10M 1/48; C10M 3/42; C10M 5/24; C10M 7/46
[52] U.S. Cl. ................. 252/32.7 E; 252/33; 252/34; 252/35; 252/39; 252/400 A
[58] Field of Search ............... 252/32.7 E, 33, 34, 252/35, 39, 400 A

[56] References Cited
U.S. PATENT DOCUMENTS

| | | | |
|---|---|---|---|
| 3,562,159 | 2/1971 | Mastin | 252/32.7 E |
| 3,726,798 | 4/1973 | Silver et al. | 252/32.7 E |
| 3,813,336 | 5/1974 | Goldschmidt | 252/32.7 E |
| 3,843,530 | 10/1974 | Niedzielski | 252/32.7 E |
| 3,898,168 | 8/1975 | Brehm | 252/32.7 E |

Primary Examiner—Delbert E. Gantz
Assistant Examiner—Irving Vaughn
Attorney, Agent, or Firm—Frank J. Sroka; Arthur G. Gilkes; William T. McClain

[57] ABSTRACT

Disclosed are a process for manufacturing metal dithiophospates, and metal dithiophosphate compositions. The process for manufacturing zinc, barium, cadmium, magnesium or nickel dithiophosphates comprises reacting phosphorus pentasulfide with one or more alcohols to form a dithiophosphoric acid; neutralizing said dithiophosphoric acid with zinc, barium, cadmium, magnesium or nickel base in the presence of an acidic promoter; and reacting a substantial portion of the excess acidic promoter with a weak base. The metal dithiophosphates and lubricating oils containing said dithiophosphates are also disclosed.

40 Claims, No Drawings

METAL DITHIOPHOSPHATE PROCESS AND/COMPOSITION

BACKGROUND

This invention relates to metal dithiophosphates, a process for their manufacture and lubricating oil compositions containing said metal dithiophosphates. More specifically, it relates to a process for the manufacture of zinc, barium, cadmium, magnesium or nickel dithiophosphates.

It is well known that various additives can be added to lubricating oils in order to improve various oil properties and to make a more satisfactory lubricant. Antiwear agents are intended to decrease wear of machine parts. Wear inhibitors for incorporation in motor oils and industrial oils are finding greater use as a result of greater stress placed on moving parts in high performance engines. Numerous additives have been developed for use in such oil compositions to improve the lubricating characteristics thereof and thereby to lessen the wear of the moving parts.

Metal diaryl and dialkyl dithiophosphates, especially zinc dithiophosphates (ZOP), have long been used as antiwear additives and antioxidants in hydraulic oils, motor oils, automatic transmission fluids and the like. In the manufacture of such metal dithiophosphates, dithiophosphoric acid is commonly neutralized with a metal base, such as zinc oxide. This neutralization step does not take place readily and commonly a large excess of the base is used in conjunction with a neutralization promoter, generally an acidic promoter. Sometimes the use of acidic promoters such as nitric acid can lead to undesirable side effects such as haze or instability. In many cases the neutralized product is difficult to filter and has a dark color.

It is an object of this invention to provide an improved process for the manufacture of metal diaryl and dialkyl dithiophosphates.

It is an object of this invention to provide a process for the manufacture of metal dithiophates wherein low excess metal base is required for the neutralization of dithiophosphoric acids.

It is an object of this invention to provide a process for the manufacture of metal diaryl dithiophosphates wherein the neutralized product does not suffer undesirable side effects caused by an acidic promoter.

It is further an object of this invention to provide a highly effective antiwear and antioxidant additive for use in lubricating oils.

SUMMARY OF THE INVENTION

Disclosed are metal dithiophosphate compositions, lubricating oil compositions containing such dithiophosphates, and a process for manufacturing such dithiophosphates.

The metal dithiophosphates comprise zinc, barium, cadmium, magnesium or nickel dithiophosphate, said dithiophosphate made by neutralization of dithiophosphoric acid with zinc, barium, cadmium, magnesium or nickel base in the presence of an acidic promoter followed by reacting a substantial portion of excess acidic promoter with a weak base.

Zinc, barium, cadmium, magnesium or nickel dithiophosphates are manufactured by a process comprising reacting a phosphoro-sulfurizing agent such as phosphorus pentasulfide, with one or more alcohols to form a dithiophosphoric acid; neutralizing said dithiophosphoric acid with zinc, barium, cadmium, magnesium or nickel base in the presence of an acidic promoter; and reacting a substantial portion of the excess acidic promoter with a weak base.

Generally phosphorus pentasulfide is reacted with alcohol at a temperature from about 100° F. to about 250° F. to form the dithiophosphoric acid. The dithiophosphoric acid is commonly neutralized at a temperature from about 100° F. to about 250° F., and the acidic promoter is reacted with a weak base at a temperature from about 100° F. to about 250° F. Preferably, the neutralization of dithiophosphoric is conducted at a temperature less than 210° F.

Commonly the molar ratio of phosphorus pentasulfide to alcohol is about 1 to 4, the molar ratio of dithiophosphoric acid to zinc, barium, cadmium, magnesium or nickel base is about 1 to 0.6, and the molar ratio of weak base to acidic promoter is about 1.5 to 1.

Acidic promoters are generally acids which form water or oil soluble metal salts or metal hydroxy salts, said metals comprising zinc, barium, cadmium, magnesium or nickel. For example, hydrochloric, perchloric and nitric acids act as promoters, where $H_3PO_3$ or HF do not.

One group of acidic promoters comprises $C_1$-$C_{10}$ carboxylic acids such as formic, acetic, propionic, butyric, pentanoic, trimetyl acetic, and the like. These acidic promoters may be hydroxy or halogen substituted such as glycolic acid, or trifluoro and trichloro acetic acids.

Another group of promoters are alkyl, alkenyl and aryl sulfonic acids. Common members of this group are $C_8$-$C_{20}$ alkyl sulfonic acids, e.g. dodecyl sulfonic acid, and benzene and alkyl benzene sulfonic acids. Suitable oil-soluble benzene sulfonic acids are the oil-soluble petroleum sulfonic acids, commonly referred to as "mahogany acids," of about 350 to 750 molecular weight, aryl sulfonic acids, and alkaryl sulfonic acids. Illustrative of such sulfonic acids are dilauryl benzene sulfonic acid, lauryl cetyl benzene sulfonic acid, paraffin-substituted benzene sulfonic acids, polyolefin alkylated benzene sulfonic acids, such as polybutylene alkylated benzene sulfonic acids in which the polybutylene substituents have molecular weight of at least about 100, and preferably within the range of from about 100 to about 10,000, and polypropylene alkylated benzene sulfonic acids in which the polypropylene substituents have a molecular weight of at least about 80 and preferably within the range of from about 80 to about 10,000. Examples of other suitable sulfonic acids are diparaffin wax-substituted phenol sulfonic acids, cetyl chlorobenzene sulfonic acids, cetyl-phenol disulfide sulfonic acids, cetyl-phenol monosulfide sulfonic acids, cetoxy capryl benzene sulfonic acids. Other suitable oil-soluble sulfonic acids are well described in the art, such as for example, U.S. Pat. Nos. 2,616,604; 2,626,207; and 2,767,209, and others.

Non-aromatic sulfonic acids are generally made by the sulfonation of most any hydrocarbyl, such as alkanes, alkenes, and the like. Also, the hydrocarbyl may contain various substitution which does not interfere with later reactions or end use. One preferred group of non-aromatic sulfonic acids is made by the sulfonation of polymers or copolymers, such as polymerized or copolymerized olefins. One such compound is sulfonated polybutene having a molecular weight in the range of about 300 to about 10,000 and containing about 0.1 to about 10 weight percent sulfur.

Metal salts of the above acids are also effective neutralization promoters, especially zinc, barium, cadmium, magnesium or nickel salts. It is especially preferred to use zinc salts in the manufacture of zinc dithiophosphates.

One preferred and commonly used promoter is nitric acid. Preferably about 0.01 to about 0.1 moles of promoter are used per mole of dithiophosphoric acid.

The weak base forms a salt with the acidic promoter and does not replace zinc, barium, cadmium, magnesium or nickel in the dithiophosphate. Many of such bases contain nitrogen such as amines and amides containing from about one to about thirty carbon atoms. Two especially preferred bases comprise ammonia and urea.

The amines can be primary, secondary or tertiary and may be straight chain branched, cyclic or aromatic. Examples of some common primary amines are ethyl, n-propyl, isopropyl, n-butyl, isobutyl, n-pentyl, isopentyl, n-hexyl, isohexyl, cyclo hexyl, n-heptyl, isoheptyl, 2-ethylhexyl and the like. Common secondary amines dimethyl, diethyl, methyl-ethyl, dipropyl, diisopropyl, dibutyl, diisobutyl, dipentyl, diisopentyl, dihexyl, diisohexyl, dicyclohexyl bis (1-methylheptyl), diheptyl, didodecyl, dioctyl, N-methyl-butyl, N-methyloctyl, N-methyloctadecyl, N-isopropyloctyl, N-methylbenzyl, and the like. In a similar manner, tertiary amines can be exemplified.

The amine may contain two or more nitrogen groups. Suitable polyamines or multifunctional amines are the following: the N-alkyl 1,3-alkylene diamines available under such names as Duomeen--for example Duomeen T, a diamine derived from tallow fatty amine and acrylonitrilo and subsequently hydrogenated, producing predominantly N-octadecyl 1,3-propane-diamine, and Duomeen C which is predominantly E-dodecyl 1,3-propane diamine-N-alkyl 1,2 alkylanediamines such as N-dodecyl 1,2-ethylene diamine; polyoxypropyleneamines such as those manufactured under their trade name POPDA-190 and POPDA-230; and 4-dodecyldiethylenetriamine. Another group of suitable amines are the ethylene or propylene polyamines. Examples of this group are diethylenetriamine, triethylene tetramine, tetraethylene pentamine, pentaethylene hexamine, dipropylene triamine, tripropylene tetramine, tetrapropylene pentamine, pentapropylene hexamine, and so on.

Suitable amides can be made by the reaction carboxylic acids with amines, especially primary amines such as those previously described. For example, acids such as maleic and succinic acids and anhydrides; alkyl and alkenyl substituted maleic and succinic acids and anhydrides; $C_1$-$C_{10}$ alkyl carboxylic acids such as formic, acetic, propionic, butyric, valeric, caproic, caprylic, and capric; dicarboxylic acids such as oxylic, glutaric, adepic, pimelic, suberic, ozelaic, sebacic, fumaric, phthalic, isophthalic, and terephthalic; and the like can be reacted with amines to form amides.

While a portion of the weak base may react with excess acid present, it is believed that a portion of the base is incorporated into the metal dithiophosphate.

Generally the molar ratio of weak base to acidic promoter is about 0.5-10:1, but preferably the molar ratio of weak base to acidic promoter is about 1-3:1.

The most commercially important metal dithiophosphates are zinc diaryl and dialkyl dithiophosphates, which are commonly used as lubricating oil additives. The zinc dialkyl dithiophosphates are generally made from alkyl alcohols containing about 3 to about 20 carbon atoms and the zinc diaryl dithiophosphate are generally made from aryl alcohols containing about 6 to about 30 carbon atoms. A phosphosulfurizing agent, such as $P_2S_5$, is reacted with the alcohol to form a dithiophosphoric acid which is then neutralized with metal base. A commonly used metal base is zinc oxide.

The process for the manufacture of metal dithiophosphate comprises reacting $P_2S_5$ with a hydroxyl compound to form a dithiophosphoric acid; and neutralizing said dithiophosphoric acid with metal base such as zinc, barium, cadmium, magnesium or nickel base, in the presence of an effective amount of a promoter.

Preferably the promoter is present at a concentration of about 0.001 to about 0.5 moles per mole of dithiophosphoric acid, more preferably about 0.11 to about 0.22 moles per mole of dithiophosphoric acid. Preferred metal bases are zinc oxide or zinc carbonate. Commonly $P_2S_5$ is reacted with the hydroxyl compound at a temperature from about 100° F. to about 250° F. and the neutralization with metal base is conducted at from about 100° F. to about 250° F.

Aryl dithiophosphates are manufactured from hydroxyl aryl compounds. These hydroxyl aryl compounds generally contain one, two or three aromatic rings but most commonly contain a single aromatic ring. Said hydroxyl aryl compounds may contain more than one hydroxy group but most commonly contain a single hydroxyl group. The aromatic ring or rings may contain various other substitutions such as hydrocarbyl, chloride, bromine, nitro and others. In some cases these substitutions do not enhance or detract from the effectiveness of the additive. In no case should the substitution interfere with the reaction with $P_2S_5$ or the neutralization step.

Commonly, hydrocarbyl substitution of the hydroxy aryl compound is desirable in order to improve the oil solubility and effectiveness of neutralized metal dithiophosphates as lubricating oil additives. Therefore, hydrocarbyl substituted hydroxy aryl compounds, such as hydrocarbyl phenols, are preferred.

The most commonly used substituted phenols contain one or more hydrocarbyl groups having about one to about 100 carbon atoms. Preferably, the hydrocarbyl groups contain about 8 to about 20 carbon atoms. The hydrocarbyl groups can be alkyl, alkenyl, aryl, aralkyl or alkaryl. Mono alkyl substitution is preferred. The hydrocarbon substitution can range from low molecular weight groups such as methyl, ethyl, propyl, isopropyl, butyl, isobutyl, and the like up to low molecular weight polymers and copolymers. Many commercially available substituted phenols contain $C_8$-$C_{20}$ substituents from polypropylene or polybutene. The hydrocarbyl substituted phenol may have other substituents, such as for example, chlorine, bromine, nitro or sulfonic acid groups.

The alkyl dithiophosphates are manufactured from hydroxy alkyl compounds such as alkyl alcohols. Metal dialkyl dithiophosphates are most commonly formed by the reaction of phosphorous pentasulfide with aliphatic alcohols to form phosphoric acid esters. The alcohols, often a mixture of alcohols, commonly contain from about 3 to about 20 carbon atoms, but preferably about 3 to about 12 carbon atoms. Sometimes dialkyl dithiophosphoric acids are represented as follows:

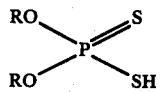

Wherein R comprises an alkyl group containing about three to about twenty carbon atoms. These alkyl groups generally originate from alcohols such as propyl, n-butyl, n-pentyl, n-hexyl, n-heptyl, n-octyl, n-decyl, n-dodecyl, hexadecyl, octadecyl or branched chain alcohols such as the methyl or ethyl branched isomers of the above. Suitable branched alcohols are isopropanol, 2-methyl-1-pentanol, 2-ethyl-1-hexanol, 2,2-dimethyl-1-octanol, and alcohols prepared from olefin oligomers such as propylene dimer or trimer by hydroboration-oxidation or by the Oxo process. It may be preferable to use mixtures of alcohols because of their low cost and possible improvement in performance.

The dialkyl or diaryl dithiophosphoric acids are generally made by reaction of about 4 moles of hydroxy compound with one mole of a phosphorous pentasulfide containing about 27 weight percent phosphorus. The phosphosulfurizing agent used is phosphorus pentasulfide. The quality of the phosphorus pentasulfide is of some importance and this reagent should have approximately the following properties:

| | |
|---|---|
| Melting point, ° F. | 270–280 |
| Wt. percent phosphorus | 25–30 |
| Wt. percent sulfur | 70–75 |
| Free of organic material. | |

The reaction is sometimes conducted in a glass-lined vessel fitted with suitable agitation equipment. Commonly, the reaction is conducted at a temperature from about 100° F. to about 250° F. for a period in the range of about 1–6 hours. The alcohol is preferably free of water.

A convenient method for controlling the end point of the reaction is to measure the specific gravity of the reaction product. The specific gravity will, of course, vary with the reaction temperature and with the excess alcohol content. The end point can also be determined by noting when the evolution of $H_2S$ ceases.

The diaryl dithiophosphoric acids are then reacted with a metal base such as zinc oxide or zinc carbonate in order to form the metal dialkyl dithiophosphate generally having a metal to phosphorus ratio of about 1–1.5:1. The neutralization reaction is usually carried out at elevated temperatures, e.g. temperatures in the range of about 100° F. to about 200°–250° F. The neutralization is effected, for example, by contacting a zinc oxide slurry with diaryl dithiophosphoric acid for a time sufficient to neutralize the acid and possibly also incorporate an excess of zinc oxide so that the material is basic. The neutralization of the aryl dithiophosphoric acids is conducted in the presence of an effective amount of a neutralization promoter. The promoter may be introduced into the neutralization reaction by being mixed with the aryl dithiophosphate prior to, during, or after the addition of metal base. The promoter may be added separately. The neutralization may usually be completed within a period of a few minutes to about 4–5 hours. The neutralized product can be used as a corrosion inhibitor without the separation of oil slurrying medium.

Metal diaryl dithiophosphates can be prepared by batch or continuous processes. In batch processes, for example, a slurry of zinc oxide in oil is charged to a reaction zone containing dihydrocarbon dithiophosphoric acid and the acid is neutralized by the zinc oxide at elevated temperatures. In continuous processing, the slurry of zinc oxide and the dihydrocarbon dithiophosphoric acid may be charged to one end of a reaction zone, e.g. the upper end of a vertical zone, maintained at elevated temperatures and the product neutralized zinc dihydrocarbon dithiophosphate may be withdrawn from the other end of the reaction zone. If desired, the product from either the batch or continuous process may be further purified by clay percolation or the like to remove insoluble components.

The oil used in the slurry is preferably a light lubricating oil; however, heavier lubricating oils can be used if desired. The lighter oils are preferred because of their lower viscosities and the greater ease of pumping such oils or slurries containing such oils. Although hydrocarbon oils and particularly petroleum oils were utilized in the procedure set out below, it is intended that other oils can also be used such as the synthetic hydrocarbon polymer oils prepared by the condensation and other methods. Ester oils are not preferred because of the possibility of their dissociation in the presence of zinc oxide under the neutralization reaction conditions. Other useable oils are the distillate fuel oils such as kerosene, heater oils, dewaxed cycle oils and the like. The light lubricating oils are particularly preferred.

One means of introducing the $P_2S_5$ into the reaction vessel is by slurrying the dry $P_2S_5$ with oil or inert slurrying agent. Sometimes it is also suitable to slurry the base, such as ZnO, in oil or neutralized metal dithiophosphorate in order to transport it to the reactor.

The lubricating oils in which the compositions of this invention are useful as additives and which comprise a major proportion of the lubricating oil compositions may be of synthetic, animal, vegetable, or mineral origin. Ordinarily mineral lubricating oils are preferred by reason of their availability, general excellence, and low cost. For certain applications, oils belonging to one of the other three groups may be preferred. Normally the lubricating oils preferred will be fluid oils, ranging in viscosity from about 40 Saybolt Universal seconds at 100° F. to about 200 Saybolt Universal seconds at 210° F. This invention contemplates also the presence of other additives in lubricating compositions. Such additives include, for example, viscosity index improving agents, pour point depressing agents, anti-foam agents, extreme pressure agents, rust-inhibiting agents, and oxidation and corrosion inhibiting agents.

The additive of this invention is generally added to lubricating oil in order to improve the antiwear or antioxidant properties of said oil. Depending on the nature of the oil, the intended use and the desired improvement, different amounts of the additive are needed in order to be effective. Generally about 0.05 to about 5 weight percent, preferably from about 0.1 to about 2 weight percent, of the additive is used.

The following examples illustrate the use of acidic promoters and weak bases in the manufacture of metal dithiophosphates.

EXAMPLE 1

317 g (1 mole) of a dithiophosphoric acid, prepared from a mixture of isobutanol, isoamylalcohol, isooctanol and $P_2S_5$ in 15 wt. % 5W oil, were neutralized by adding dropwise dithiophosphoric acid to a slurry of 47 g (0.57 m) ZnO and 0.32 ml (0.005 m) nitric acid (70%) in 20 g 5W oil at 175° F.

After addition of the acid, sweetness was checked (absence of $H_2S$) with lead acetate paper. If a base is to be added, it would be added at this point in the procedure. In this case, none is added.

The reaction mixture was heated to 200° F. Simultaneously, nitrogen was blown through the mixture to remove the water formed during the neutralization. The reaction mixture was then filtered through diatomic earth. The recovered filtrate contained 9.3% zinc, 8.45% phosphorus, and 18.2% sulfur.

EXAMPLE 2

To the product of Example 1, 1.0 ml (0.015 m) $NH_4OH$ (28%) was added as base to the stirred reaction mixture. After 15 minutes, nitrogen was blown through the mixture and water was stripped off. At the same time, the temperature was raised to 200° F. To the waterfree reaction mixture 10 g of filter cell was added. Filtration through filter cell yielded a clear, light brown oil.

EXAMPLE 3

The procedure of Example 1 was used except the neutralization promoter was 0.38 ml (0.005 m) HCl (38%).

EXAMPLE 4

To the product of Example 3, 1.0 ml (0.015 m) $NH_4OH$ (28%) was added as base following the procedure in Example 2.

EXAMPLE 5

The procedure of Example 1 was followed except 2.5 g (0.01 m) zinc sulfoxylate dissolved in 2 ml water, was added as a promoter after two thirds of the dithiophosphate had been dropped to the ZnO slurry.

EXAMPLE 6

To the product of Example 5, 2.0 ml (0.03 m) $NH_4OH$ was added as base after complete neutralization of the dithiophosphoric acid following the procedure in Example 2.

EXAMPLE 7

The procedure of Example 1 was followed except 3.8 g (0.01 m) zinc acetate was used as neutralization promoter.

EXAMPLE 8

To the product of Example 7, 2.0 ml (0.03 m) $NH_4OH$ was added as base following the procedure of Example 2.

EXAMPLE 9

The procedure of Example 1 was followed except 0.32 ml (0.005 m) $HNO_3$ (70%) was used as promoter.

EXAMPLE 10

To the product of Example 9, 0.6 g (0.01 m) urea was dissolved in 1.5 ml $H_2O$ was added as base following the procedure of Example 2.

EXAMPLE 11

The procedure of Example 1 was followed except 0.32 ml (0.005 m) $HNO_3$ (70%) was used as promoter.

EXAMPLE 12

To the product of Example 11, 1.5 ml (0.15 m) triethylamine was added as base following the procedure of Example 2.

EXAMPLE 13

The procedure of Example 1 was followed except the dithiophosphoric acid was prepared from a mixture of isopropyl, isobutyl and isooctyl alcohols, and 0.32 ml (0.005 m) $HNO_3$ (70%) was used as promoter.

EXAMPLE 14

To the product of Example 13, 0.6 g (0.01 ml) urea was dissolved in 1.5 ml of water, was added as base following the procedure of Example 2.

EXAMPLE 15

184 g (0.25 m) of a dithiophosphoric acid in 25 weight percent 5W oil, prepared from nonyl phenol and $P_2S_5$, was neutralized by adding dropwise the aromatic dithiophosphoric acid to a slurry of 42 g ZnO and 0.6 ml (0.01 mol) acetic acid in 30 g 5W oil. The reaction temperature was maintained at 160° F. After addition of the acid sweetness of the mixture was tested with lead acetate paper. If base is to be added, it is added at this point in the procedure. In this case, none is added.

The reaction mixture was heated to 220° F. and the water of neutralization stripped by a stream of nitrogen. After addition of diatomic earth the mixture was filtered. The recovered filtrate contained 3.3% zinc, 2.75% phosphorus and 5.3% sulfur.

EXAMPLE 16

To the stirred reaction mixture from Example 15, 2.04 ml (0.03 m) $NH_4OH$ (28%) was added as base and allowed to react for 30 min. Water was then stripped off by blowing with $N_2$. At the same time, the temperature was raised to 220° F. After addition of filter cell, the mixture was filtered through diatomic earth.

EXAMPLE 17

The procedure of Example 15 was followed except 5.0 g (0.02 m) zinc sulfoxylate dissolved in 4 ml water was used as promoter.

EXAMPLE 18

To the product of Example 17, 3.03 ml (0.05 m) $NH_4OH$ (28%) was added as base following the procedure of Example 16.

EXAMPLE 19

The procedure of Example 15 was followed except 6.0 ml (0.01 m) zinc fluoborate (40% aqueous solution) was used as promoter.

EXAMPLE 20

To the product from Example 19, 2.04 ml (0.03 m) $NH_4OH$ (28%) was added as base following the procedure of Example 16.

EXAMPLE 21

The procedure of Example 15 was followed except 1.27 ml (0.02 m) $HNO_3$ (70%) was used as promoter.

EXAMPLE 22

To the product of Example 21, 3.03 ml (0.05 m) NH₄OH (28%) was added as base following the procedure of Example 16.

EXAMPLE 23

The procedure of Example 15 was followed except 3.8 g (0.01 m) zinc octoate was added as promoter.

EXAMPLE 24

To the product of Example 23, 2.04 ml (0.03 m) NH₄OH (28%) was added as base following the procedure of Example 16.

EXAMPLE 25

The procedure of Example 15 was followed except 1.27 ml (0.02 m) HNO₃ (70%) was used as promoter.

EXAMPLE 26

To the product of Example 25, 1.8 g urea (0.03 m) dissolved in 4 ml water, was added as base following the procedure of Example 16.

EXAMPLE 27

The procedure of Example 15 was followed except 1.27 ml (0.02 m) HNO₃ (70%) was used as promoter.

EXAMPLE 28

To the product of Example 27, 2 g magnesium hydroxide (0.035 m) suspended in 5 ml water was added as base following the procedure of Example 16.

The effect of weak base treatment on acid promoted neutralized zinc dithiophosphates in regard to hydrolytic stability and deposit formation was demonstrated by heating the sample to 160° F for 48 hours and then allowing the sample to stand at room temperature for a period of time.

EFFECT OF BASE TREATMENT OF HYDROLYTIC STABILITY AND DEPOSIT FORMATION

EFFECT OF BASE TREATMENT OF HYDROLYTIC STABILITY AND DEPOSIT FORMATION

Aliphatic ZOP from i-C₄H₉OH, i-C₅H₁₁OH, i-C₈H₁₂OH

| Ex. No. | Catalyst | Base | Appearance After Heating to 160° F. For 48 Hrs. and Standing at Room Temperature for Three Months |
|---|---|---|---|
| 1 | HNO₃ | — | Sweet, hazy, light deposits |
| 2 | HNO₃ | NH₄OH | Sweet, clear, no deposits |
| 3 | HCl | — | Sour, deposits |
| 4 | HCl | NH₄OH | Sweet, no deposits |
| 5 | Zn Sulfoxylate | — | Sour, light deposits |
| 6 | Zn Sulfoxylate | NH₄OH | Sweet, clear, no deposits |
| 7 | Zn Octoate | — | Sour, deposits |
| 8 | Zn Octoate | NH₄OH | Sweet, clear, no deposits |
| 9 | HNO₃ | — | Sweet, deposits |
| 10 | HNO₃ | Urea | Sweet, clear, no deposits |
| 11 | HNO₃ | — | Sweet, deposits |
| 12 | HNO₃ | Triethylamine | Sweet, clear, no deposits |

Aliphatic ZOP From i-C₃H₇OH, i-C₄H₉OH, i-C₈H₁₇OH

| 13 | HNO₃ | — | Sour, heavy deposits |
| 14 | HNO₃ | Urea | Sweet, clear, no deposits |

Aromatic ZOP From Nonyl Phenol

| Ex. No. | Catalyst | Base | Appearance After Heating to 240° F. for 72 Hrs. |
|---|---|---|---|
| 15 | Acetic Acid | — | Sweet, hazy, deposits |
| 16 | Acetic Acid | NH₄OH | Sweet, clear, no deposits |
| 17 | Zn Sulfoxylate | — | Sour, hazy, deposits |
| 18 | Zn Sulfoxylate | NH₄OH | Sweet, clear, no deposits |
| 19 | Zn Fluoborate | — | Sour, hazy, deposits |
| 20 | Zn Fluoborate | NH₄OH | Sweet, clear, no deposits |
| 21 | HNO₃ | — | Sweet, hazy, deposits |
| 22 | HNO₃ | NH₄OH | Sweet, clear, no deposits |
| 23 | Zn Octoate | — | Sour, hazy, deposits |
| 24 | Zn Octoate | NH₄OH | Sweet, clear, no deposits |

The effect of base treatment on acid promoted zinc dithiophosphates in regard to loss of basicity was demonstrated by comparing basicity before and after heating to 240° F. for 72 hours. The concentration of basic zinc dithiophosphates was determined by the following procedure: 2 g of an aromatic zinc dithiophosphate was dissolved in 25 ml benzonitrile and 25 ml ethylene dichloride and 6-9 ml 0.1 N perchloric acid in dioxane was added. The solution was titrated with 0.1N KOH in methanol in the presence of bromthymol as indicator (M. Kolobielski, CCL Report No. 320, February, 1973).

LOSS OF BASICITY BY HAZE AND DEPOSIT FORMATION IN NONYL PHENOL ZOP

LOSS OF BASICITY BY HAZE AND DEPOSIT FORMATION IN NONYL PHENOL ZOP

| | | % Basic Compound | |
|---|---|---|---|
| Ex. | Neutralization Promoter | Before | After |
| | | Heating to 240° F for 72 Hrs. | |
| 19 | Zn Fluoborate | 47.6 | 42.8 |
| 23 | Zn Octoate | 50.3 | 42.8 |
| 21, 25 | HNO₃ | *49.0 | *35.5 |
| 26 | HNO₃ treated with urea | 49.0 | 49.0 |

*Average

The effect of base treatment on acid promoted zinc dithiophosphates in regard to anti-wear properties of the ZOP was demonstrated by the Shell Four Ball test.

FOUR BALL TEST OF ALIPHATIC ZOP**

Oil Formulation: 5W Oil

Test Conditions: 1800 rpm, 190° F., 1 Hour.

FOUR BALL TEST OF ALIPHATIC ZOP**
Oil Formulation 5W Oil
Test Conditions: 1800 rpm, 190° F., 1 Hour.

| Ex. | ZnDTP** Wt. % | Catalyst | Base | Wear Scar Diameter (mm) 40 Kg | 60 Kg |
|---|---|---|---|---|---|
| 9 | 1 | HNO₃ | — | | 0.93 |
| 10 | 1 | HNO₃ | Urea | | 0.86 |
| 9 | 0.5 | HNO₃ | — | | 0.91 |
| 10 | 0.5 | HNO₃ | Urea | | 0.84 |
| 1 | 1 | HNO₃ | — | .60*** | |
| 2 | 1 | HNO₃ | NH₄OH | .57*** | |

** ZnDTP prepared from i-BuOH, i-C₅H₁₁OH, i-C₈H₁₇OH
*** 2 hour test period.

FOUR BALL TEST OF AROMATIC ZOP****

Oil Formulation 5 W Oil

Test Conditions: 1800 rpm, 190° F, 1 Hr., 60 Kg

FOUR BALL TEST OF AROMATIC ZOP****
Oil Formulation 5W Oil
Test Conditions: 1800 rpm, 190° F, 1 Hr., 60 Kg

| Example | ZnDTP, Wt. % | Catalyst | Base | Wear Scar Diameter (mm) |
|---------|--------------|----------|------|-------------------------|
| 25 | 1 | HNO₃ | — | 2.2 |
| 26 | 1 | HNO₃ | Urea | 2.0 |

**** ZnDTP prepared from nonyl phenol

I claim:

1. A lubricating oil composition comprising a major proportion of a lubricating oil and an effective amount of an oil soluble antiwear additive, said additive comprising a zinc, barium, cadmium, magnesium or nickel dithiophosphate, said dithiophosphate made by neutralization of dithiophosphoric acid with zinc, barium, cadmium, magnesium or nickel base in the presence of an acidic promoter followed by reacting a substantial portion of excess acidic promoter with a weak base.

2. The composition of claim 1 wherein the dithiophoshphate is a zinc dithiophosphate.

3. The composition of claim 2 wherein the dithiophosphate is a zinc dialkyldithiophosphate.

4. The composition of claim 2 wherein the dithiophosphate is a zinc diaryldithiophosphate.

5. The composition of claim 2 wherein dithiophosphoric acid is neutralized with zinc oxide.

6. The composition of claim 1 wherein the acidic promoter is nitric acid.

7. The composition of claim 1 wherein the molar ratio of weak base to acidic promoter is about 0.5-10:1.

8. The composition of claim 7 wherein the molar ratio of weak base to acidic promoter is about 1-3:1.

9. The composition of claim 1 wherein the weak base forms a salt with the acidic promoter and does not replace the zinc, barium, cadmium, magnesium or nickel in the dithiophosphate.

10. The composition of claim 9 wherein the weak base contains nitrogen.

11. The composition of claim 10 wherein the base comprises ammonia or urea.

12. The composition of claim 1 wherein the additive is present at a concentration of about 0.05 to about 5 weight percent.

13. The composition of claim 12 wherein the additive is present at a concentration of about 0.1 to about 3 weight percent.

14. The composition of claim 1 wherein the lubricating oil has a viscosity from about 40 Saybolt Universal seconds at 100° F. to about 200 Saybolt Universal seconds at 210° F.

15. A process for the manufacture of zinc, barium, cadmium, magnesium or nickel dithiophosphate comprising reacting phosphorus pentasulfide with one or more alcohols to form a dithiophosphoric acid; neutralizing said dithiophosphoric acid with zinc, barium, cadmium, magnesium or nickel base in the presence of an acidic promoter; and reacting a substantial portion of the excess acidic promoter with a weak base.

16. The process of claim 15 for the manufacture of zinc dithiophosphate.

17. The process of claim 15 wherein the phosphorus pentasulfide is reacted with alcohol at a temperature from about 100° F. to about 250° F., the dithiophosphoric acid is neutralized at a temperature from about 100° F. to about 250° F., and the acidic promoter is reacted with a weak base at a temperature from about 100° F. to about 250° F.

18. The process of claim 15 wherein the molar ratio of phosphorus pentasulfide to alcohol is about 1 to 4, the molar ratio of dithiophosphoric acid to zinc, barium, cadmium, magnesium or nickel base is about 1 to 0.6, and the molar ratio of weak base to acidic promoter is 1.5 to 1.

19. The process of claim 15 wherein the alcohol comprises alkyl alcohols.

20. The process of claim 19 wherein the alcohol contains about 3 to about 20 carbon atoms.

21. The process of claim 15 wherein the alcohol comprises aryl alcohols.

22. The process of claim 21 wherein the alcohol contains about 6 to about 30 carbon atoms.

23. The process of claim 15 wherein the dithiophosphoric acid is neutralized with zinc oxide or carbonate.

24. The process of claim 15 wherein the promoter is nitric acid.

25. The process of claim 15 wherein about 0.001 to about 0.5 moles of promoter are used per mole of dithiophosphoric acid.

26. The process of claim 15 wherein the weak base forms a salt with the acidic promoter and does not replace zinc, barium, cadmium, magnesium or nickel in the dithiophosphate.

27. The process of claim 26 wherein the base contains nitrogen.

28. The process of claim 27 wherein the base comprises ammonia or urea.

29. A process for the manufacture of zinc, barium, cadmium, magnesium or nickel dithiophosphates comprising reacting one mole phosphorus pentasulfide with about four moles of alcohol to form a dithiophosphoric acid; combining said dithiophosphoric acid with zinc, barium, cadmium, magnesium or nickel base in the presence of an acidic promoter to form a neutralization mixture and neutralizing said dithiophosphoric acid; and adding a weak base to the neutralization mixture after the neutralization is essentially complete.

30. A composition comprising zinc, barium, cadmium, magnesium or nickel dithiophosphate, said dithiophosphate made by neutralization of dithiophosphoric acid with zinc, barium, cadmium, magnesium or nickel base in the presence of an acidic promoter followed by reacting a substantial portion of excess acidic promoter with a weak base.

31. The composition of claim 30 wherein the dithiophosphate is a zinc dithiophosphate.

32. The composition of claim 30 wherein the dithiophosphate is a zinc dialkyldithiophosphate.

33. The composition of claim 31 wherein the dithiophosphate is a zinc diaryldithiophosphate.

34. The composition of claim 31 wherein dithiophoric acid is neutralized with zinc oxide.

35. The composition of claim 30 wherein the acidic promoter is nitric acid.

36. The composition of claim 30 wherein the molar ratio of weak base to acidic promoter is about 0.5-10:1.

37. The composition of claim 36 wherein the molar ratio of weak base to acidic promoter is about 1-3:1.

38. The composition of claim 30 wherein the weak base forms a salt with the acidic promoter and does not replace the zinc, barium, cadmium, magnesium or nickel in the dithiophosphate.

39. The composition of claim 38 wherein the weak base contains nitrogen.

40. The composition of claim 39 wherein the base comprises ammonia or urea.

* * * * *